(12) United States Patent
Campion

(10) Patent No.: US 7,585,291 B1
(45) Date of Patent: Sep. 8, 2009

(54) EYE COLORING SYSTEMS

(76) Inventor: Michael Campion, 1635 W. Oakland St., Chandler, AZ (US) 85224

( * ) Notice: Subject to any disclaimer, the term of this patent is extended or adjusted under 35 U.S.C. 154(b) by 0 days.

(21) Appl. No.: 12/167,946

(22) Filed: Jul. 3, 2008

(51) Int. Cl.
*A61M 35/00* (2006.01)
*A61M 31/00* (2006.01)
*A61F 2/14* (2006.01)

(52) U.S. Cl. ............... 604/289; 623/4.1; 604/521

(58) Field of Classification Search ............. None
See application file for complete search history.

(56) References Cited

U.S. PATENT DOCUMENTS

| | | | |
|---|---|---|---|
| 4,582,402 A * | 4/1986 | Knapp ............ | 351/162 |
| 4,870,964 A * | 10/1989 | Bailey et al. ............ | 606/6 |
| 5,793,466 A | 8/1998 | Moncada | |
| 6,004,302 A * | 12/1999 | Brierley ............ | 604/264 |
| 6,306,127 B2 | 10/2001 | Homer | |
| 6,367,480 B1 | 4/2002 | Coroneo | |
| 6,372,449 B1 | 4/2002 | Coroneo | |
| 6,533,769 B2 | 3/2003 | Holmen | |
| 6,692,256 B2 | 2/2004 | Snyder et al. | |
| 2003/0159615 A1 * | 8/2003 | Anderson et al. ......... | 106/31.03 |
| 2003/0175324 A1 * | 9/2003 | Robinson et al. ............ | 424/427 |

OTHER PUBLICATIONS

Marriam-Webster, online dictionary, "coat", accessed Sep. 15, 2008.*
Jacobs et al (Ophthalmology, vol. 113, Iss 4 (2006) 707-713).*
Author Unknown, Damn Cool Pics: Eye Tattoo, http://damncoolpics.blogspot.com/2007/07/eye-tattoo.html, Jul. 11, 2007. Applicant makes no representation regarding the factuality of this article.

* cited by examiner

*Primary Examiner*—Frederick Krass
*Assistant Examiner*—Benjamin Packard
(74) *Attorney, Agent, or Firm*—Keith L. Jenkins, Registered Patent Attorney, LLC; Keith L. Jenkins

(57) ABSTRACT

A novel system for coloring the human eye is presented, including methods of coloring the conjunctiva on its internal or external surface, coloring the sclera, coloring the iris, suspending colorant in the subconjunctival space, and combinations of two or more of these methods. The system avoids tattooing, implanting, and corneal modification. Permanent results may be obtained. Colorants may be coverings, suspensions, or stains.

1 Claim, 8 Drawing Sheets

EYE COLORING SYSTEMS

FIELD OF THE INVENTION

The present invention relates to systems (methods, apparatuses, and their relationships) for changing the color of the eye, perhaps permanently, for cosmetic purposes. It is not related to tattooing or to implants, nor to modifications of the cornea.

BACKGROUND OF THE INVENTION

The human eye is a generally spherical structure, or eyeball, of a living tissue called "sclera," which is normally white. An opening in the front of the eye, called a pupil, permits entry of light into the eyeball, through the lens of the eye and onto the retina. The size of the pupil is controlled by an iris, which has a natural color. When reference to a person's eye color is made in day-to-day conversation, it is normally the color of the iris that is referred to. In front of the pupil and iris is the cornea. Covering the front of the eyeball and the inner linings of the eyelids is a thin transparent tissue called the conjunctiva. The conjunctiva is normally moist and can move relative to the sclera upon which it rests. The space underneath the conjunctiva (such as between the conjunctiva and the sclera) is called the "subconjunctival space".

An attempt at eye coloration that was widely reported involved eye tattooing, in which, with some 40 needle pricks, a blue ink was introduced into the subconjunctival space of the eye for purposes of body ornamentation. The methodology was dangerous and the results are still not completely known. That is, reports of whether or not the eye tattoo volunteer went blind are pending.

U.S. Pat. No. 5,793,466 was issued to Moncada on 1998 Aug. 11 for an EYE COLOR HIGHLIGHTING CONTACT LENS that features a contact lens with patterns of colored radial lines outside a central clear circular area. The contact lens is removable.

Several patents have been issued for surgical contrast coloration methods that assist the surgeon in visualizing tissues of eye. U.S. Pat. No. 6,306,127 was issued to Horner on 2001 Oct. 23 for a METHOD OF ALTERATION OF IRIS PIGMENTATION that features using laser beams of various frequencies to destroy selected pigments in the iris and thereby change the color of the iris. U.S. Pat. No. 6,692,526 was issued to Snyder, et al., on 2004 Feb. 17 for a OPTHALMOLOGICAL SURGERY COLORANT AND DELIVERY SYSTEM that features the use of a temporary, selectively administered, contrast stain in retinal and cataract surgery to aid the surgeon in distinguishing various tissues of the eye. U.S. Pat. No. 6,367,480 issued to Coroneo on 2002 Apr. 9 for METHODS FOR VISUALIZING THE ANTERIOR LENS CAPSULE OF THE HUMAN EYE features use of trypan blue for enhanced visualization of the anterior lens capsule during cataract surgery. U.S. Pat. No. 6,372,449 issued to Coroneo on 2002 Apr. 16 for OPTHALMIC METHODS AND USES features the use of trypan blue to identify membranes and structures within the eye. U.S. Pat. No. 6,533,769 issued to Holmen on 2003 Mar. 18 for METHOD FOR USE IN CATARACT SURGERY features the use of active agents to destroy epithelial cells during cataract surgery and provides for a dye accompanying the active agents to assist the surgeon in visualizing the active agents during introduction and subsequent removal of the active agents and the dye. The existing surgical methods are primarily focused on enhancing the surgeon's ability of visualize the tissues, are short term methods, and are not directed towards cosmetic surgery. Colored implants are known in eye surgery (see US20060036318 A1 to Foulkes published 2006 Feb. 16 and 7037337 B2 to Carriazo 2006 May 2). Staining a cornea in a healthy eye is also known (WO1995003017 to Robbins, et al., published 1995 Feb. 2).

The inventor, an ophthalmologist, has recognized a need for an improved cosmetic eye coloring system that does not introduce the risks of eye tattooing, implanting, or corneal modification. In order to meet those needs, and to solve related problems, the inventor has developed the novel eye coloring system of the present invention.

OBJECTS AND FEATURES OF THE INVENTION

A primary object and feature of the present invention is to provide an eye coloring system that will be safe. A further primary object and feature of the present invention is to provide such a system that enables coloring of the sclera, the surfaces of the conjunctiva, the anterior surface of the iris, as well as the safe coloring of the subconjunctival space. A further primary object and feature of the present invention is to provide such a system that does not include lasers, implants, or corneal modification. Other objects and features of this invention will become apparent with reference to the following descriptions.

SUMMARY OF THE INVENTION

In accordance with a preferred embodiment hereof, this invention provides an improved method for coloring of the eye including at least one of coloring the external surface of the conjunctiva; suspending a colorant in the subconjunctival space using a single needle insertion and distribution of the colorant within the subconjunctival space by means of exerting pressure on the conjunctiva; coloring the sclera; and coloring the iris. The improved method may further include the step of distributing the colorant in a predetermined pattern. The steps of coloring include a surface application of at least one colorant. The steps of coloring include the step of drying the surface to be colored before application of the at least one colorant. The step of coloring may include applying at least two different colors to different portions of the surface. The colorants are sterile. The steps of coloring and suspending include sterile procedures. Colorants may be stains or surface coatings.

The improved method of coloring the eye includes coloring the external surface of the conjunctiva including the steps of anesthetizing such eye with a topical anesthetic; securing such eyelids in a spaced-apart relationship using an eyelid speculum; drying the external surface of such conjunctiva to be colored; applying a colorant to said dried external surface of such conjunctiva; drying said colorant on said external surface of such conjunctiva; removing said eyelid speculum; and applying at least one of antibiotic and anti-inflammatory drops to such eye.

The improved method of coloring the eye, wherein the step of suspending a colorant in the subconjunctival space comprises the steps of anesthetizing such eye with a topical anesthetic; securing such eyelids in a spaced-apart relationship using an eyelid speculum; preparing colorant by mixing with balanced salt solution; drawing said prepared colorant into a syringe having an approximately 30 gauge needle; injecting said prepared colorant into such subconjunctival space; applying pressure to the conjuntiva proximate said injected prepared colorant to distribute said injected prepared colorant to desired portions of such subconjunctival space; removing said eyelid speculum; and applying at least one of antibiotic and anti-inflammatory drops to such eye.

The improved method of coloring the eye, wherein the coloring the sclera includes the steps of: anesthetizing such eye with at least one of a topical anesthetic, a standard retro bulbar anesthesia, and a peribulbar anesthesia; securing such eyelids in a spaced-apart relationship using an eyelid speculum; providing additional magnification of a portion of such sclera to be colored; dissecting such conjunctiva over said portion of such sclera to be colored; drying the portion of such sclera to be colored; applying a colorant to the dried portion of such sclera; drying the applied colorant; closing the conjunctiva over the colored portion of such sclera; applying at least one of antibiotic and anti-inflammatory drops to such eye; and removing said eyelid speculum.

The improved method of coloring the eye, wherein the step of coloring the iris comprises the steps of anesthetizing such eye with at least one of a topical anesthetic, a retro bulbar anesthesia, and a peribulbar anesthesia; securing such eyelids in a spaced-apart relationship using an eyelid speculum; providing additional magnification of a portion of such iris to be colored; constricting such pupil of such eye using one of a pre-operative miotic and an intra-operative miotic; making first and second incisions into the anterior chamber of such eye on opposite sides of the cornea of such eye; removing residual aqueous from the angle of the anterior chamber proximate such edge of such pupil using a cannula, while avoiding damage to other interocular structures; drying a portion of such iris of such eye by concurrently infusing a blowing gas through said first incision and aspirating said blowing gas through said second incision at a rate that maintains inflation of such eye but does not over-inflate such eye; applying colorant to such iris of such eye; drying such applied colorant; exchanging said blowing gas with balanced salt solution; providing interocular pressure in the physiologic range; applying at least one of antibiotic and anti-inflammatory drops to such eye; and removing the eyelid speculum.

An improved method for coloring of the eye using sterile procedures and colorants, the method including the steps of accessing a surface of such eye to be colored; drying said surface of such eye; and applying a colorant to the dried surface. The method further includes the step of drying the at least one colorant after applying the colorant. The method wherein the accessing step includes surgical access. The method wherein the accessing step includes inflation of a space between the surface and a membrane overlying said surface. The method wherein inflation uses a mixture of gases. The method wherein the colorant includes a surface coating.

An improved method for coloring of the eye using sterile procedures and colorants, the method comprising the steps of drying a surface of such eye; and applying at least one colorant to the dried surface. The method wherein drying includes either drying with a sponge or drying with blown gas. The method further including the step of drying the colorant after the step of applying, wherein drying comprises drying with blown gas.

BRIEF DESCRIPTION OF THE DRAWINGS

The above and other objects and advantages of the present invention will become more apparent from the following description taken in conjunction with the following drawings in which.

DETAILED DESCRIPTION OF THE BEST MODES AND PREFERRED EMBODIMENTS OF THE INVENTION

Figure 1:
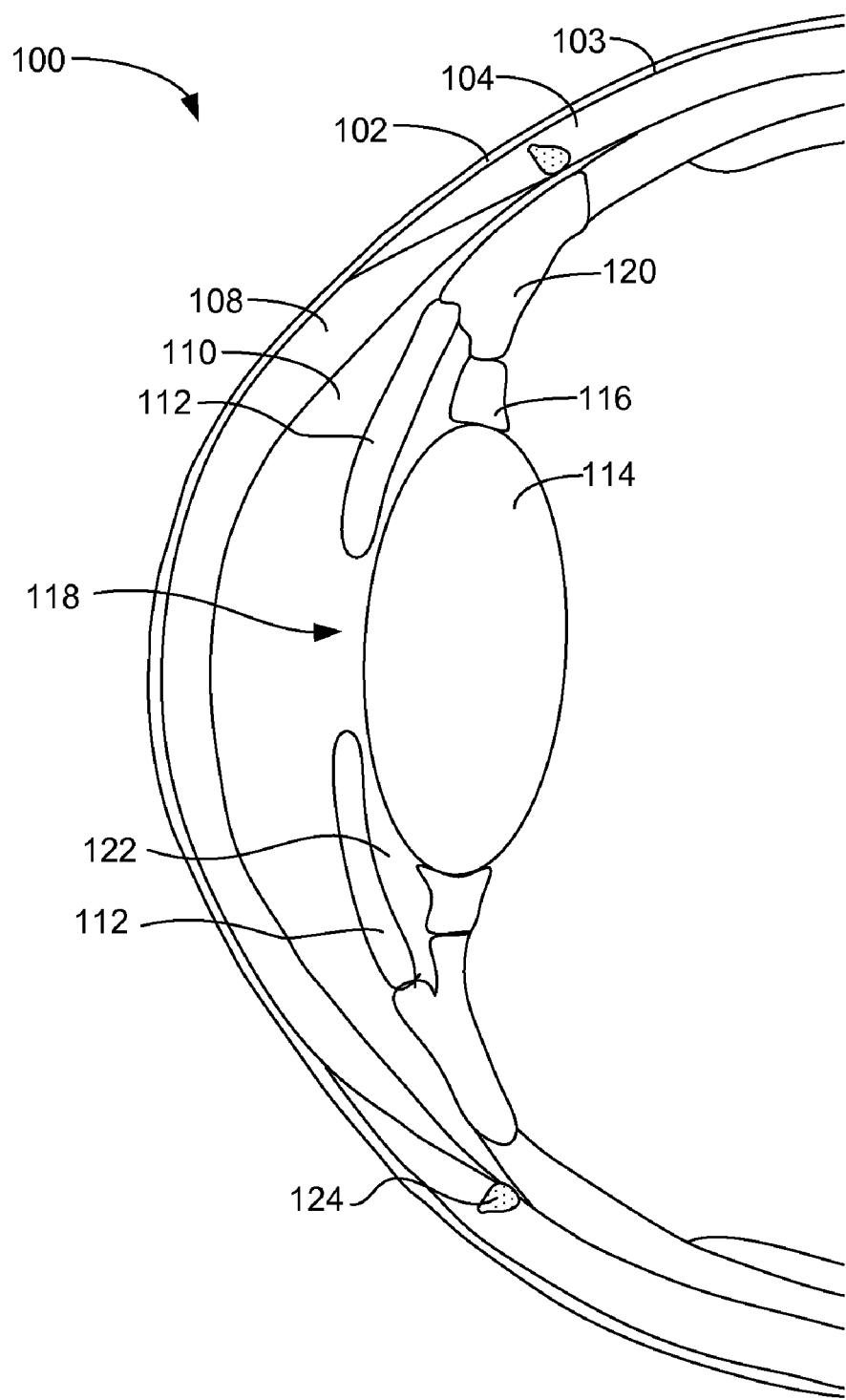
FIG. 1 shows a side elevation cross-sectional view illustrating relevant portions of an eye as a reference.

FIG. 1 shows a side elevation cross-sectional view illustrating relevant portions of an eye 100 as a reference. The front of the eye 100 is surrounded by the conjunctiva 102, which covers the cornea 108 and the sclera 104. Between the conjunctiva 102 and the sclera 104 or cornea 108 is the subconjunctival space 103. Normally, the subconjunctival space 103 is very narrow and contains a thin layer of fluid. Behind the cornea 108 lies the anterior chamber 110, normally filled with an aqueous humor. The iris 112 is a sphincter surrounding the pupil 118. The iris 112 regulates the amount of light that moves through the pupil 118 to the lens 114. Lens 114 is encapsulated and the capsule is suspended in place by the suspensory ligaments 116. The suspensory ligaments 116 and the iris 112 are maintained in position by the ciliary body 120. The posterior chamber 122 is located behind the iris 112. Just beyond the cornea 108 and near the ciliary body 120 is the trabecular meshwork 124.

Figure 2:
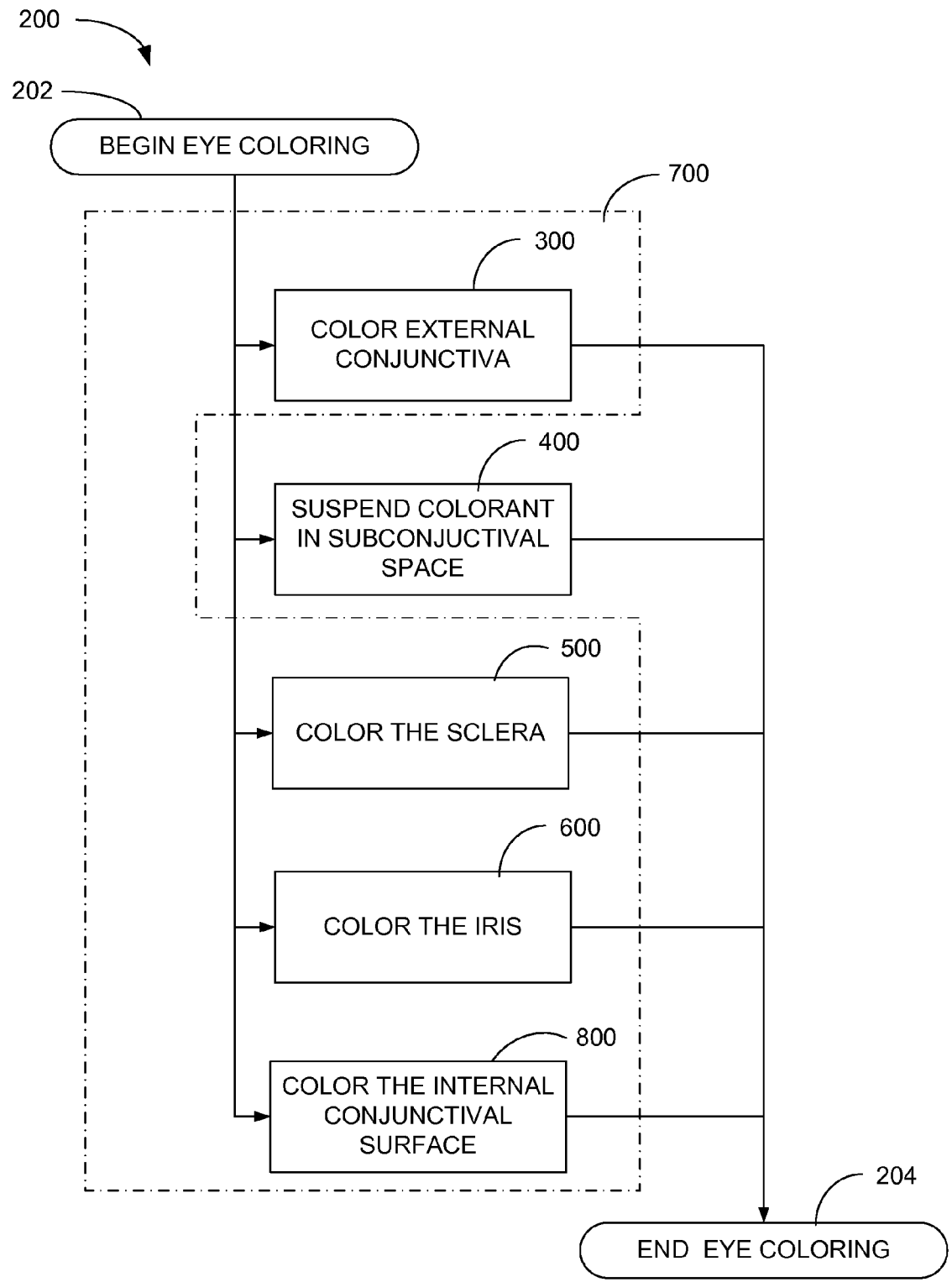
FIG. 2 shows a process flow diagram illustrating an improved eye-coloring system, according to a preferred embodiment of the present invention.

FIG. 2 shows a process flow diagram illustrating an improved eye-coloring system 200, according to a preferred embodiment of the present invention. The step 202 includes providing necessary materials and instruments for the following steps. Depending on the method 300, 400, 500, 600, or 800 to be followed, the following materials and instruments may be needed: topical anesthetic eye drops; injectable ophthalmic anesthesia; intraocular miotic; pilocarpine eye drops; antibiotic eye drops; anti-inflammatory eye drops; cotton tip applicators; ophthalmic operating microscope; surgical loupes; eyelid speculum; ocular sponges; sterile gauzes; compressed gas, commercially available tank or handheld can; coloring agents, various types; paint brush; ophthalmic lacrimal probe(s); syringes; needles, various sizes; ocular cannulas, various sizes ophthalmic scissors; ophthalmic forceps; ophthalmic sutures, various sizes and materials; ophthalmic cautery, various kinds; surgical glue; sterile ophthalmic drape; cataract removal machine (phacoemulsification ("phaco") machine); sterile tubing for above machine; infusion/aspiration probe for above machine; and balanced salt solution. Following step 202, any one particular step 300, 400, 500, 600, or 800, or any combination of two or more of steps 300, 400, 500, 600, or 800, may be performed. Each of these steps 300, 400, 500, 600, or 800 will be described in more detail below. Step 700 is a generalization of the surface-coloring steps 300, 500, 600, and 800. Some inadvertent surface coloring may occur in step 400. Surface coloring may include surface coating. Step 204 includes equipment cleaning, disposal of surgical waste, putting away unused portions of colorant, and other steps needed to secure the medical facility and provide post-surgical care for the patient.

Figure 3:
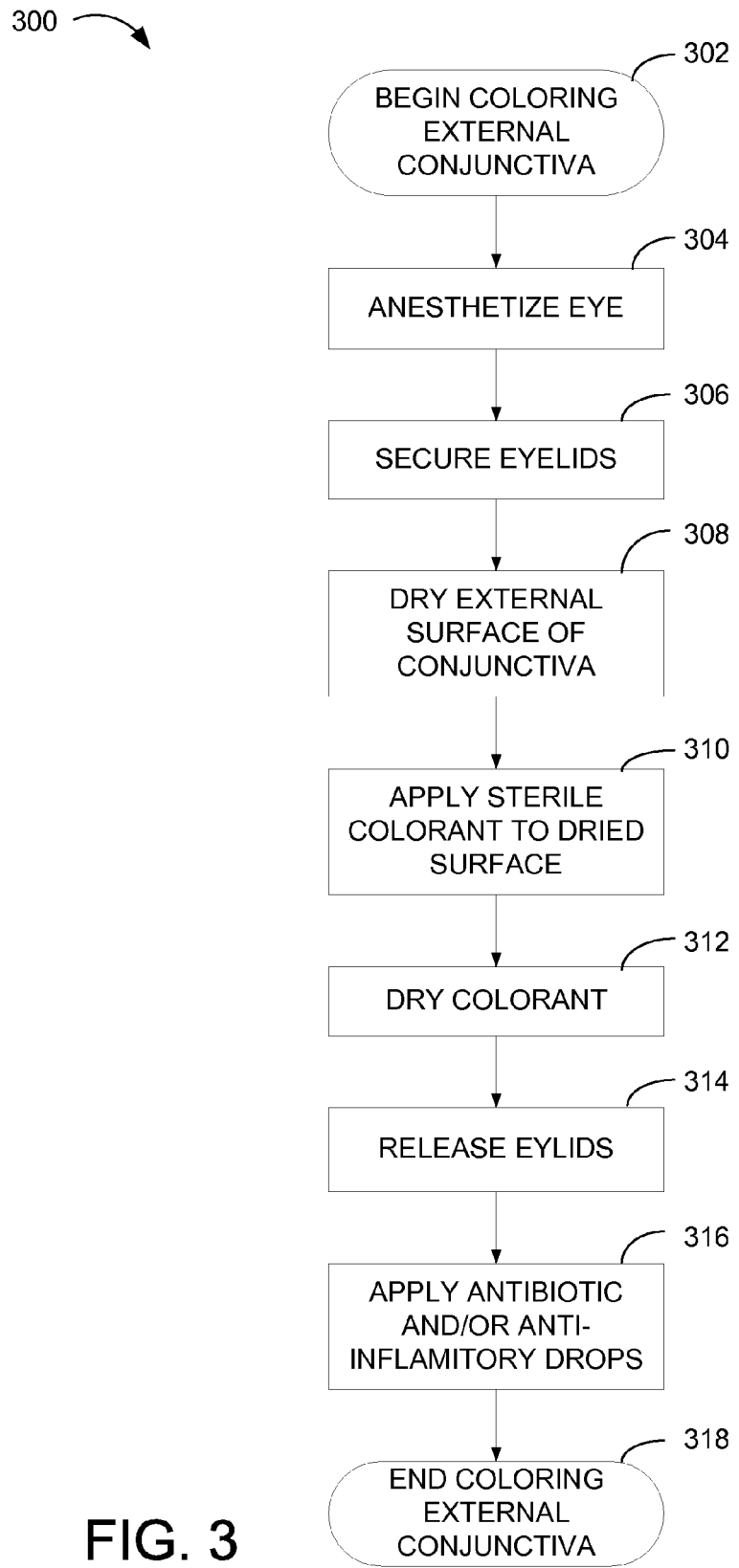
FIG. 3 shows a process flow diagram illustrating an exemplary method of coloring the external surface of the conjunctiva as part of an improved eye-coloring system, according to a preferred embodiment of the present invention.

FIG. 3 shows a process flow diagram illustrating an exemplary method 300 of coloring the external surface of the conjunctiva 102 as part of an improved eye-coloring system 200, according to a preferred embodiment of the present invention. Step 302 includes identification of the area of the external surface of the conjunctiva 102 to be colored, selection of any pattern that may be used, and selection of the colors to be used. Step 302 may also include testing for allergic reaction to any of the colorants selected. In step 304, the eye 100 is anesthetized in ways known in the art of ophthalmic surgery. Minimally intrusive anesthetic methods are preferred, but consideration of patient allergies and sensitivities is also important. Preferably, a topical anesthetic, such as tetracaine 1% is used in step 304. A deeper anesthesia may be developed by soaking a cotton-tipped applicator and then placing the soaked swab in contact with the conjunctiva 102 for a time. In step 306, the eyelids are secured in an open, or spaced apart, position using an eyelid speculum.

The selected portion of the surface of the conjunctiva 102 is dried in step 308, using a sponge or blown dry gas. The dry gas may be a single gas, such as nitrogen, or a mixture of gasses, such as air. In step 310, sterile colorant is applied to the dried external surface of the conjunctiva 102. Application of the sterile colorant may be by any type of applicator including, without limitation, droppers, swabs, brushes, pens, and sprayers. A stencil may be used during step 310. Colorants, because they are being introduced to the eye 100, are preferably sterile. In step 312, the colorant is dried on the external surface of the conjunctiva 102. Step 312 may include removing excess colorant by sponge and then using blown dry gas to dry the colorant. Once the colorant has dried, the eyelids are released by removal of the eyelid speculum in step 314. Antibiotic and/or anti-inflammatory drops may be given in step 316 either after the eyelid speculum is removed, as shown, or before the eyelid speculum is removed. Step 318 may include a period of observation for any sensitivity, and verification that eyesight has not been impaired.

Those of skill in the art, enlightened by the present disclosure, will appreciate that various colorants may be applied to various portions of the external surface of the conjunctiva 102 to form patterns. Likewise, those of skill in the art, enlightened by the present disclosure, will appreciate that the colorants may be permanent, such as inks used in tattooing, or temporary, such as food coloring.

The method 300 of the present invention represents an improvement over eye tattooing, in that it requires no needle insertions into the eye 100. The method 300 of the present invention represents an improvement over surgical contrast dying in that method 300 may be permanent and is cosmetic.

Figure 4:
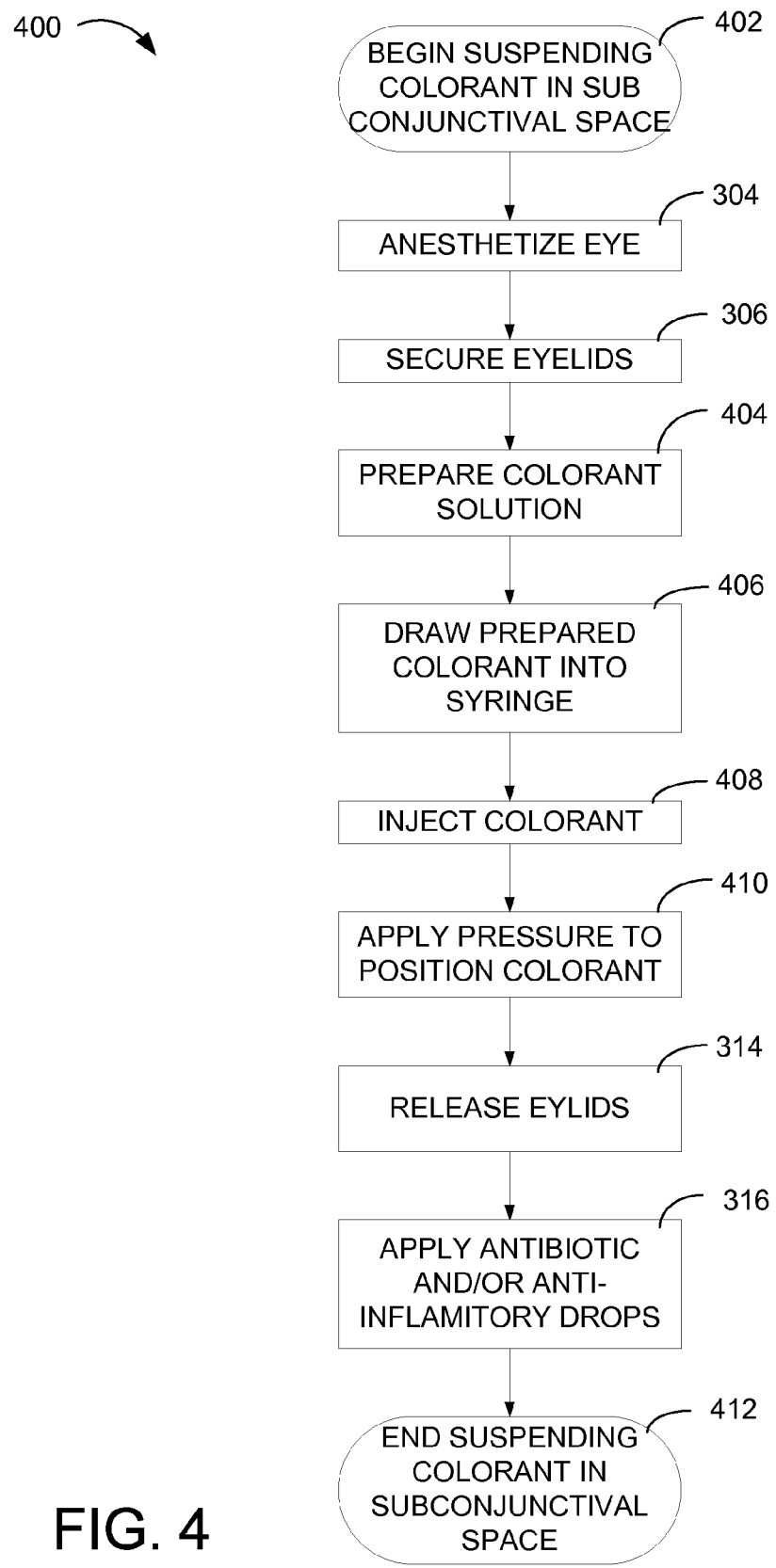
FIG. 4 shows a process flow diagram illustrating an exemplary method of suspending colorant in the subconjunctival space as part of an improved eye-coloring system, according to a preferred embodiment of the present invention.

FIG. 4 shows a process flow diagram illustrating an exemplary method 400 of suspending colorant in the subconjunctival space 103 as part of an improved eye-coloring system 200, according to a preferred embodiment of the present invention. Step 402 includes identification of the area of the external surface of the conjunctiva 102 to be colored, selection of any pattern that may be used, and selection of the colors to be used. Step 402 may also include testing for allergic reaction to any of the colorants selected. In step 304, the eye 100 is anesthetized in ways described above. In step 306, the eyelids are secured in an open position using an eyelid speculum. In step 404, the sterile colorant solution is prepared by, for example, dilution with a balanced salt solution to achieve the desired color saturation. The prepared colorant is drawn into a syringe in step 406 having an approximately 30-gauge needle and slowly injected into the subconjunctival space 103 at a single site in step 408. While the colorant is being injected, pressure is applied 410 with a cotton-tipped applicator or equivalent, to pressure the prepared colorant solution to move within the subconjunctival space 103 to spread the colorant solution completely through the subconjunctival space 103 or to form a pattern in the subconjunctival space 103. The steps 404, 406, 408, and 410 may be repeated for various colors in the course of one step 400. Once the colorant has been positioned, the eyelids are released by removal of the eyelid speculum in step 314. Antibiotic and/or anti-inflammatory drops may be given in step 316 either after the eyelid speculum is removed, as shown, or before the eyelid speculum is removed. Step 412 may include a period of observation for any sensitivity, and verification that eyesight has not been impaired. Subconjunctival space 103 is an intraocular space.

Those of skill in the art will appreciate that suspending colorant in the subconjunctival space 103 may cause coloration of the internal surface of the conjunctiva 102 and of the outer surface of the sclera 104. If the colorant used contains various pigments that are taken up differentially by the internal surface of the conjunctiva 102 and the outer surface of the sclera 104, interesting results may be obtained. In a particular embodiment of the method, a first colored pattern may be established in the subconjunctival space 103 as a background, and a second colored pattern may be established on the external surface of the conjunctiva 102 as a foreground image, with the combination producing striking results. For example, and without limitation, a sun-ray pattern in gold, with smooth reflective particles in the gold colorant may be established in the subconjunctival space 103 and a pale blue colorant may be established on the external surface of the conjunctiva 102, creating one visual effect (from the perspective of another) in bright light and another visual effect in dim light. Those of skill in the art of color overlays, enlightened by this disclosure, will appreciate the vast number of overlay patterns that may be achieved on the human eye 100.

The method 400 of the present invention represents an improvement over eye tattooing, in that it requires only one needle insertion for each colored area, and not the 40 needle insertions used in tattooing. The method 400 of the present invention represents an improvement over surgical contrast dying in that method 400 may be permanent and is cosmetic.

Figure 5:
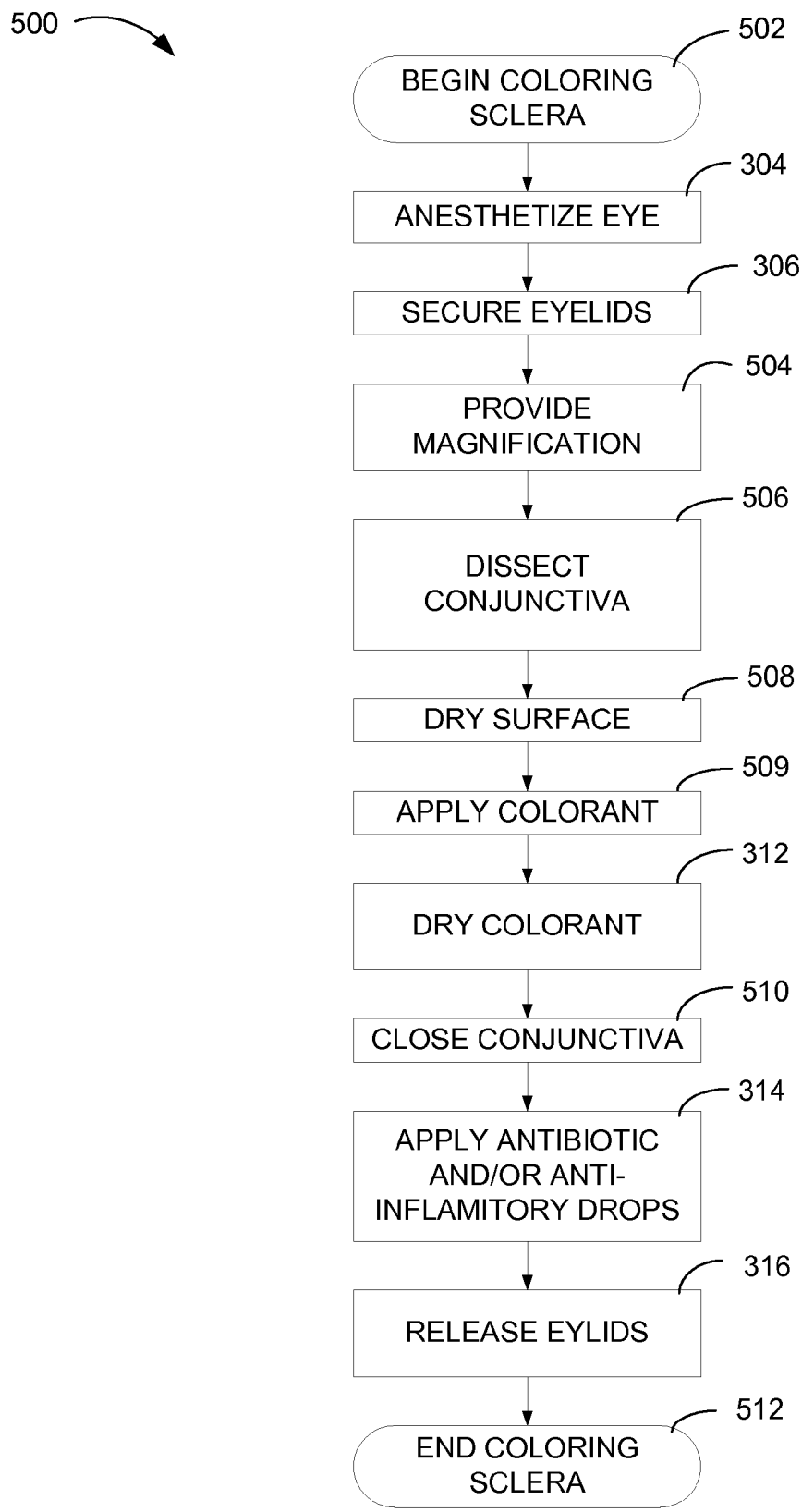
FIG. 5 shows a process flow diagram illustrating an exemplary method of coloring the sclera as part of an improved eye-coloring system, according to a preferred embodiment of the present invention.

FIG. 5 shows a process flow diagram illustrating an exemplary method 500 of coloring the sclera 104 as part of an improved eye-coloring system 200, according to a preferred embodiment of the present invention. Step 502 includes identification of the area of the external surface of the sclera 104 to be colored, selection of any pattern that may be used, and selection of the colors to be used. Step 502 may also include testing for allergic reaction to any of the colorants selected. In step 304, the eye 100 is anesthetized in ways described above. In some embodiments, standard retro bulbar or peribulbar anesthesia may be used similar to other eye surgeries. In step 306, the eyelids are secured in an open position using an eyelid speculum. In step 504, the physician employs a surgical microscope to more precisely observe steps 506, 508, 509, 312, and 510. In step 506, the conjunctiva 102 is dissected to expose the portion of the surface of the sclera 104 to be colored. Step 506 may be accomplished using Westcot scissors with forceps or equivalent surgical technique. In step 508, the surface of the sclera 104 to be colored is dried, using a sponge or blown dry gas. In step 509, sterile colorant is applied to the dried surface of the sclera 104 and then the colorant is dried in step 312, as discussed more fully above. After the colorant has dried 509, the conjunctiva 102 is closed 510 over the site or sites using standard ophthalmic techniques, such as suturing, cautery, medical glue, and the like. Once the conjunctiva 102 has been closed 510, the eyelids are released by removal of the eyelid speculum in step 314. Antibiotic and/or anti-inflammatory drops may be given in step 316 either after the eyelid speculum is removed, as shown, or before the eyelid speculum is removed. Step 512 includes all steps necessary to verify the finished procedure and to secure the surgical environment. A colorant may be a stain or a surface coating.

Those of skill in the art, enlightened by the present invention, will appreciate the vast number of combinations of techniques that may be employed. For example, and without limitation, a colored background or pattern may be first established on the sclera 104 using method 500. After the sclera 104 has healed, a colorant that is at least partially transparent but which contains smooth reflective particles may be suspended in the subconjunctival space 103 using method 400, and a colored pattern may be established on the front surface of the conjunctiva 102 to provide a decorative cosmetic effect.

The method 500 is an improvement over eye tattooing because it colors the sclera 104 without tattooing.

Figure 6:
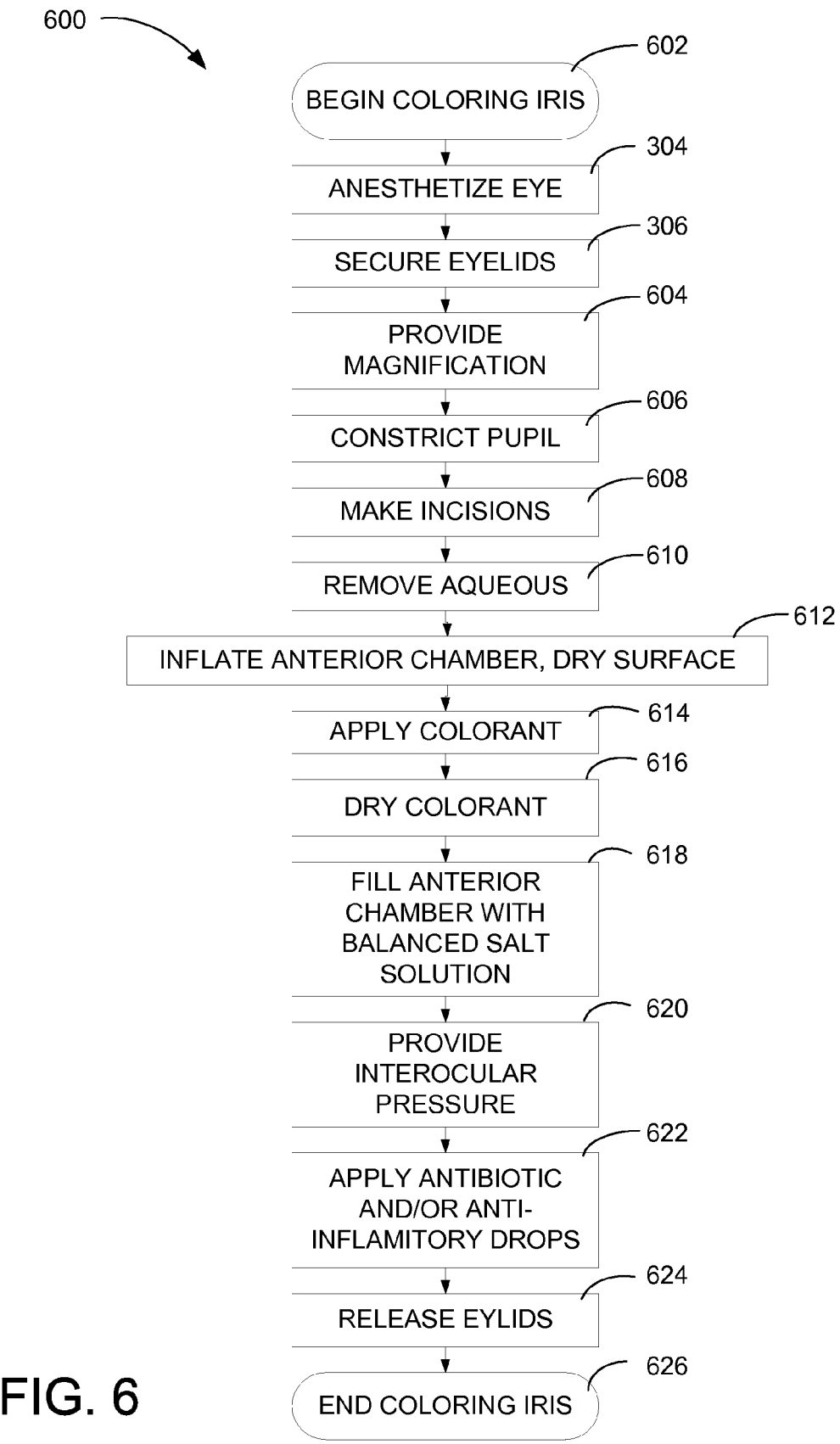
FIG. 6 shows a process flow diagram illustrating an exemplary method of coloring the iris as part of an improved eye-coloring system, according to a preferred embodiment of the present invention.

FIG. 6 shows a process flow diagram illustrating an exemplary method 600 of coloring the iris 112 as part of an improved eye-coloring system 200, according to a preferred embodiment of the present invention. Step 602 includes identification of the area of the external surface of the iris 112 to be colored, selection of any pattern that may be used, and selection of the colors to be used. Step 602 may also include testing for allergic reaction to any of the colorants selected. In step 304, the eye 100 is anesthetized in ways discussed above, including standard retro bulbar or peribulbar anesthesia. In step 306, the eyelids are secured in an open position using an eyelid speculum. In step 604, a surgical microscope or surgical loupe is used to provide magnification. In step 606, the pupil 118 is constricted. Preferably, the pupil 118 is constricted pre-operatively with pilocarpine drops. In an alternative embodiment of the method 600, an interoperative miotic, such as Miochol is used for step 606. In step 608, two incisions are made into the anterior chamber 110 on opposite sides of the cornea 108. An air bubble is injected into the anterior chamber 110 to displace the aqueous humour, which is removed 610 from the angle of the anterior chamber 110 and near the edge of pupil 118 using a small gauge cannula. Care is exercised to avoid damage to other interocular structures such as the lens 114, the cornea 108, and trabecular meshwork 124. Anterior chamber 110 is an intraocular space.

In step 612, the surface of the iris 112 is dried. To accomplish drying 612 of the iris 112, a probe, similar to those used to infuse and aspirate fluid in cataract surgery, is used to infuse dry gas into the anterior chamber 110 and to aspirate the dry gas at the same time. The flow rates of infusion and aspiration are regulated to maintain inflation of the anterior chamber 110. A phaco machine, known in the art of ophthalmic surgery, may be used to provide the infusion and aspiration of dry gas. In an alternative embodiment, the supply of dry gas may come from a commercially available tank, through a regulator coupled to the tank. Standard tubing may be used to connect the gas supply to the probe in the eye 100. Over-inflation of the anterior chamber 110, as well as under inflation of the anterior chamber 110, is to be avoided. The probe is manipulated with one hand to aim the blowing dry gas onto the surface to be colored and, thereby, to dry that surface. A colorant may be a stain or a surface coating.

In step 614, the colorant is applied to the dried surface of the iris 112. Preferably, a lacrimal probe, known in the art of ophthalmic surgery, is held in the surgeon's other hand and used to apply the sterile colorant to the surface of the iris 112. The gas infusion probe is used to dry the colorant, in step 616, immediately after it is applied. Once the colorant is applied and dried, the lacrimal probe is removed. The gas in the eye 100 is gently exchanged with balanced salt solution to maintain inflation of the anterior chamber 110. The interocular pressure is checked and finally established in the correct physiologic range. In step 622 antibiotic and/or anti-inflammatory drops are placed on the eye 100, and the eyelids are released in step 624 by removing the eyelid speculum.

Those of skill in the art, enlightened by the present invention, will appreciate the coloring and patterning schemes that may be used on an iris 112, and many practical, as well as decoratively cosmetic, purposes for this invention. Those of skill in the art, enlightened by the present invention, will appreciate that the infusion and aspiration technique described for coloring the iris 112 is an alternate technique for coloring the inside surface of the conjunctiva 102 and/or the outside surface of the sclera 104, by inflating the subconjunctival space 103 and applying colorant to the interior of the inflated area.

Method 600 is an improvement over eye tattooing because the iris is not penetrated.

Figure 7:
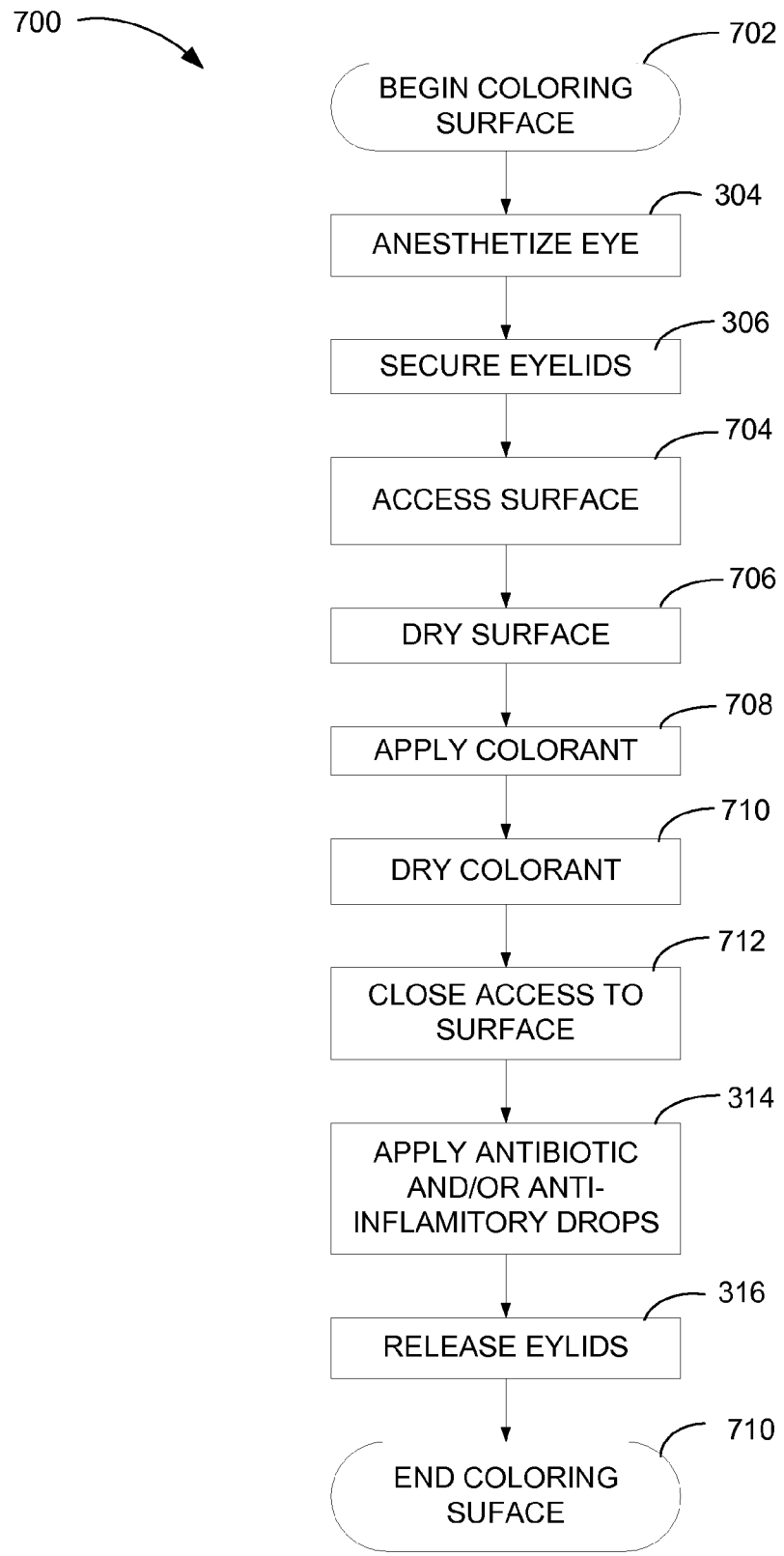
FIG. 7 shows a process flow diagram illustrating an exemplary general method of coloring a surface of the eye as part of an improved eye-coloring system, according to a preferred embodiment of the present invention.

FIG. 7 shows a process flow diagram illustrating an exemplary general method 700 of coloring a surface of the eye 100 as part of an improved eye-coloring system 200, according to a preferred embodiment of the present invention. The coloration of any eye surface begins with preparatory step 702, which subsumes the preparatory steps 302, 502, 602, and 802. Steps 304 perform the same function throughout, although there are different specific techniques for different levels of invasiveness of the procedure. Steps 306 are the same throughout, although none require any particular model or type of eyelid speculum. Each method 300, 400, 500, 600, and 800 requires gaining surgical access 704 to the surface to be colored. The complexity of this step varies with the method 300, 400, 500, 600, or 800, but all methods require gaining access 704. In each method 300, 500, 600, and 800, the surface to be colored must be dried 706. In method 400, a portion of the colorant may adhere to the interior surface of the conjunctiva 102 and to the outer surface of the sclera 104. In any event, the facing surfaces of the sclera 104 and conjunctiva 102 are accessed in method 400 even if only to create the subconjunctival space 103 that holds the colorant. Step 706 subsumes various drying techniques, including those described above relating to steps 308, 508, 612, and 804 such as blown gas, sponge, or blotter techniques. Step 706 is not used in method 400. Step 708 subsumes steps 310 (used in method 300, 500, and 800) and 614, as well as various additional application techniques appropriate to this invention. Step 710 subsumes steps 312 (used in method 300, 500, and 800) and 616, as well as various additional colorant drying techniques appropriate to this invention. In step 712, access to the surface is closed. Step 712 subsumes steps 314, 510, 618 & 620, and 806, as well as various additional closure techniques appropriate to this invention. Step 314 performs the same function throughout methods 300, 400, 500, 600, and 800, although the particular type, composition, and concentration of antibiotic drops or anti-inflammatory drops may vary. Step 316 performs the same function throughout methods 300, 400, 500, 600, and 800. Step 710 has the same function as steps 318, 412, 512, 626, and 804, although the particulars may vary.

Method 700 is an improvement over eye tattooing because the colorant is applied to a surface, rather then injected.

Figure 8:
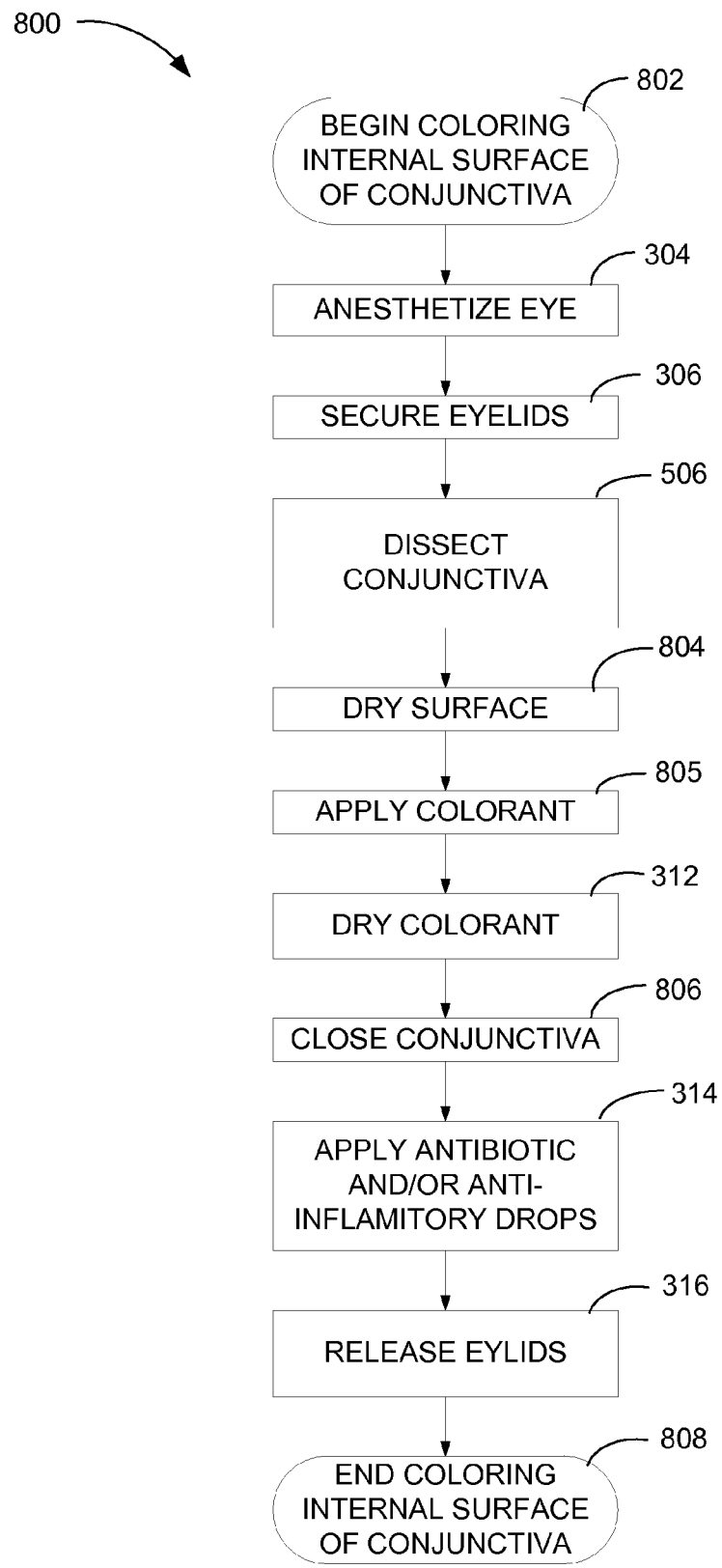
FIG. 8 shows a process flow diagram illustrating an exemplary method of coloring the internal surface of the conjunctiva as part of an improved eye-coloring system, according to a preferred embodiment of the present invention.

FIG. 8 shows a process flow diagram illustrating an exemplary method 800 of coloring the internal surface of the conjunctiva 102 as part of an improved eye-coloring system 200, according to a preferred embodiment of the present invention. Preparatory step 802 is similar to the preparations in step 502, with the possible exception of the selection of colorant type. Steps 304 and 306 are discussed above under method 500. In step 504, magnification is provided for improving visualization of the site. In step 506, the conjunctiva 102 is dissected and laid open to show its underside. The surface of the underside of the conjunctiva 102 is dried, in step 508, using blown dry gas or a sponge. In step 805, sterile colorant is applied to the interior, or underside, surface of the conjunctiva 102. The colorant is then dried in step 312, using gently blown dry gas and optionally, a sponge or blotter. The conjunctiva 102 is closed in step 806, using known surgical closures. Steps 314 and step 316 are as previously described. The method ends with step 808, which may include verification of the patient's eyesight and securing the surgical environment. A colorant may be a stain or a surface coating.

Method 800 is an improvement over eye tattooing because it enables coloring only the interior surface of the conjunctiva 102 and does not require 40 needle insertions.

All of the methods 300, 400, 500, 600, 700, and 800 are improvements over surgical contrast coloring because surgical contrast coloring is not permanent, patterned, or cosmetic. All of the methods 300, 400, 500, 600, 700, and 800 are distinct from tattooing an ossified cornea 108, because the methods 300, 400, 500, 600, 700, and 800 can be used on eyes 100 that are not blind and do not modify the cornea 108. All of the methods 300, 400, 500, 600, 700, and 800 are preferably sterile procedures and are steps of improved eye-coloring system 200. The steps of each method 300, 400, 500, 600, 700, and 800 are preferably used in combination and in order to achieve the desired results. Each method 300, 400, 500, 600, 700, and 800 engages colorant on natural surfaces of the eye 100 and none require destruction or removal of eye tissues.

Although the present inventor has described his preferred embodiments of this invention, it will be understood that the broadest scope of this invention includes modifications such as variations in the patterns and colors as well as some variation in ophthalmic surgical equipment and supplies. For example, and without limitation, the teachings of this disclosure may be applied to mammalian eyes generally. Likewise, the teachings of this disclosure may be applied for cosmetic surgery to recover normal appearance lost to accident or diseases of the eye. Further, the teachings of this disclosure may be applied to identification markings, such as may be colored onto the conjunctiva 102 inside the lower eyelid. Such scope is limited only by the below claims as read in connection with the above specification. Further, many other advantages of applicant's invention will be apparent to those skilled in the art from the above descriptions and the below claims.

What is claimed is:

1. A method of cosmetically coloring a human eye, wherein said method comprises the steps of:
   a) anesthetizing said eye with at least one of a topical anesthetic, retro bulbar anesthesia, and peribulbar anesthesia;
   b) securing the eyelids in a spaced-apart relationship using an eyelid speculum;
   c) providing additional magnification of a portion of the iris to be colored;
   d) constricting the pupil of said eye using a pre-operative miotic or an intra-operative miotic;
   e) making first and second incisions into the anterior chamber of said eye on opposite sides of the cornea of said eye;
   f) removing aqueous residue from the angle of said anterior chamber proximate the edge of said pupil using a cannula, while avoiding damage to other interocular structures;
   g) drying a portion of said iris of said eye by concurrently infusing a blowing gas through said first incision and aspirating said blowing gas through said second incision at a rate that maintains inflation of said eye but does not over-inflate said eye;
   h) applying colorant to said iris of said eye;
   i) drying said applied colorant;
   j) exchanging said blowing gas with balanced salt solution;
   k) providing interocular pressure in the physiologic range;
   l) applying at least one of antibiotic and anti-inflammatory drops to said eye; and
   m) removing said eyelid speculum.

* * * * *